(12) United States Patent
McLaughlin

(10) Patent No.: US 6,274,122 B1
(45) Date of Patent: Aug. 14, 2001

(54) DEVICE AND METHOD USING DRY MIXTURES FOR WHITENING TEETH

(76) Inventor: Gerald McLaughlin, 12 Cottonwood Ave., Port Jefferson Station, NY (US) 11776

( * ) Notice: Subject to any disclaimer, the term of this patent is extended or adjusted under 35 U.S.C. 154(b) by 0 days.

(21) Appl. No.: 09/312,935

(22) Filed: May 17, 1999

Related U.S. Application Data

(60) Provisional application No. 60/114,976, filed on Jan. 7, 1999.

(51) Int. Cl.[7] ............... A61K 7/16; A61K 7/20; A61C 5/00; A61G 17/02

(52) U.S. Cl. ............... 424/53; 424/49; 433/80; 433/215; 433/216; 128/860; 128/861; 128/862

(58) Field of Search ............... 424/53; 433/80, 433/215, 216; 128/860, 861, 862

(56) References Cited

U.S. PATENT DOCUMENTS

| | | | |
|---|---|---|---|
| 3,337,466 | * | 8/1967 | Puetzer et al. ............ 252/99 |
| 3,372,125 | * | 3/1968 | Hill ............ 252/99 |
| 3,601,321 | * | 8/1971 | Barth et al. ............ 241/3 |
| 3,793,211 | * | 2/1974 | Kohlhepp et al. ............ 252/99 |
| 4,064,062 | * | 12/1977 | Yurko ............ 252/99 |

(List continued on next page.)

FOREIGN PATENT DOCUMENTS

| | | |
|---|---|---|
| WO97/11676 | 4/1997 | (WO) . |
| WO97/21419 | 6/1997 | (WO) . |

Primary Examiner—Shep K. Rose
(74) Attorney, Agent, or Firm—Klarquist Sparkman Campbell Leigh & Whinston, LLP

(57) ABSTRACT

A device is provided for the treatment of teeth including an outer layer of non-porous polymeric material forming a trough, an inner layer forming an inner lining of the trough, and a treatment layer including a treatment agent disposed between the outer layer and the inner layer. The inner layer allows penetration of the treatment agent through after an aqueous solution is introduced to the device. A device is provided for the treatment of teeth including an outer layer of non-porous polymeric material in the form of a trough, wherein the trough has an outside and an inside surface. An outer lining layer is proximate to the inside surface of the outer layer; the outer lining layer includes a material for retaining a treatment agent. An inner lining layer forms an inner lining of the trough, wherein the inner lining layer includes a water-permeable material. A treatment layer is disposed between the inner lining layer and the outer lining layer, wherein the treatment layer includes a treatment agent. A method is provided for bleaching teeth or dentures of a subject. The method includes providing a laminated device having a trough for the treatment of the teeth of the subject, wherein the device includes an outer layer of non-porous polymeric material in the form of a trough, an inner layer forming an inner lining of the trough, and a treatment layer including a treatment agent disposed between the outer layer and the inner layer. An aqueous solution is added to the laminated device, and the teeth or dentures of the subject in are placed in the device. A method of treating a tooth is provided, including capturing a treatment agent between a liner and a trough; and introducing an aqueous solution, thereby inducing the penetration of said treatment agent through said liner to treat the tooth. A composition is provided for the whitening of a tooth including a dry form of a gel forming agent and a bleaching agent. A laminated device is provided that has a trough for the treatment of the teeth of a subject, wherein the device includes a first layer of non-porous polymeric material in the form of a trough and a premeasured amount of a composition for whitening of a tooth including a dry form of a gel forming agent and a bleaching agent.

33 Claims, 2 Drawing Sheets

U.S. PATENT DOCUMENTS

| | | | |
|---|---|---|---|
| 4,180,467 | * 12/1979 | Barth | 252/99 |
| 4,422,950 | * 12/1983 | Kemper et al. | 252/186.38 |
| 4,990,089 | 2/1991 | Munro | 433/215 |
| 5,032,178 | 7/1991 | Cornell | 106/35 |
| 5,264,205 | 11/1993 | Kelly | 424/53 |
| 5,302,374 | 4/1994 | Wagner | 424/52 |
| 5,403,578 | 4/1995 | Gordon | 424/53 |
| 5,437,858 | 8/1995 | Hungerbach et al. | 424/53 |
| 5,476,607 | * 12/1995 | Eoga et al. | 252/99 |
| 5,575,654 | 11/1996 | Fontenot | 433/215 |
| 5,645,428 | 7/1997 | Yarborough | 433/215 |
| 5,648,064 | 7/1997 | Gaffar et al. | 424/53 |
| 5,827,505 | * 10/1998 | Hughes et al. | 424/49 |
| 5,863,202 | 1/1999 | Fontenot et al. | 433/215 |
| 5,942,152 | * 8/1999 | Tafesh et al. | 252/186.39 |
| 5,980,249 | 11/1999 | Fontenot | 433/215 |
| 5,989,526 | * 11/1999 | Aaslyng et al. | 424/50 |
| 6,064,538 | * 12/1999 | Hughes et al. | 424/49 |

* cited by examiner

DEVICE AND METHOD USING DRY MIXTURES FOR WHITENING TEETH

CROSS REFERENCE TO RELATED APPLICATION

This application claims priority from U.S. Provisional Application Ser. No. 60/114,976, filed Jan. 7, 1999, which is incorporated by reference in its entirety.

FIELD OF THE INVETION

The present invention relates to the field of dentistry, and specifically to the whitening of the teeth.

BACKGROUND OF THE INVENTION

Teeth generally become more darkly pigmented with age and exposure to materials such as tea and coffee, and it has long been a goal of dentistry to provide a means to safely and effectively reverse this darkening process. Historically there are two approaches to the problem. The first involves removing pigmentation that has adhered onto the surface of the teeth. The conventional techniques commonly use abrasives, sometimes augmented with solvents. While rapidly effective, these techniques have the disadvantage of only being able to remove external stains, leaving all internal pigmentation unchanged. Thus, the whitening effect is extremely limited.

A second technique involves a method of using oxidizing agents to penetrate into the tooth structure and bleach out the undesired pigmentation. The active agents are usually either weak solutions of carbamide peroxide or hydrogen peroxide.

At present, the method of application of the whitening agent utilizes either custom or stock dental trays that are shaped to hold a separate aqueous composition containing the bleaching agent against the teeth to be whitened. The trays are filled with gel or liquid peroxide, and worn for long periods of time, sometimes even overnight. After a series of lengthy treatments, the teeth usually begin to show the desired whitening effect.

While effective on both external and internal discolorations, one major problem encountered with the custom stock dental trays and the aqueous solutions stems from the materials used. All of the aqueous solutions of peroxide ("wet" peroxides) begin to break down and lose effectiveness with time. One particularly useful active agent utilized in such compositions is formed from the combination of water and granular urea peroxide. When granular urea peroxide is isolated from moisture and humidity it has a extremely long shelf life, but once mixed with water it breaks down to urea and hydrogen peroxide and immediately begins to degrade. Although this degradation is desirable while in use—since it is the reaction products that causes the bleaching effect—it is undesirable during shipping and storage. An attempt to overcome this limitation has been made by adding gelling agents such as Carbopol, Pemulan, and the like, to the urea peroxide solution. Although the gels extend the useful life of the peroxide, they also slow down its effectiveness during use. Some products. cannot be shipped during certain times of the year or over weekends as they loose too much potency during the shipping period due to temperature variations. Thus, most of the products currently on the market require use within a short time after manufacture and often require refrigeration during storage.

Another problem of the current moist whitening agents in use is that they cannot be conveniently carried by the customer for fear of leakage from the packaging. Leakage of a bleach material into the surrounding area of a pocketbook, pocket, or briefcase can be disastrous.

In general, the most effective application of conventional whitening agents is by placement in a custom-formed tooth stent or tray. Unfortunately this normally requires an additional visit to the dentist, and will require the patient to endure the tooth impression procedure. In addition, the cost of the extra material and labor can be significant.

Alternatively, some people use the pre-mixed gels in a stock or non-custom tray. Unfortunately the fit of the stock trays to the teeth is imprecise and the bleaching gel rapidly leaks from the tray. It is for this reason that the effectiveness of the stock trays currently in use is limited: after a very short time the bleaching agent will leak out leaving insufficient active ingredient in the tray. In addition to being inefficient, this configuration causes the patient to swallow a much larger amount of bleaching agent than necessary.

SUMMARY OF THE INVENTION

In light of the foregoing, it is apparent that there is a need in the art to simply and comfortably whiten teeth with materials that are not sensitive to storage conditions or time. In addition, it is desirable to create a material that is in a dry phase prior to use so that the chances of mishap from leakage are minimized. In addition, it is desirable to design a system of delivery that uses stock parts but which eliminates the excessive leakage found when using the present system.

A device is provided for the treatment of teeth including an outer layer of non-porous polymeric material forming a trough, an inner layer forming an inner lining of the trough, and a treatment layer including a treatment agent disposed between the outer layer and the inner layer. The inner layer allows penetration of the treatment agent through the inner layer after an aqueous solution is introduced to the device.

A device is provided for the treatment of teeth including an outer layer of non-porous polymeric material in the form of a trough, wherein the trough has an outside and an inside surface. An outer lining layer is proximate to the inside surface of the outer layer; the outer lining layer includes a material for retaining a treatment agent. An inner lining layer forms an inner lining of the trough, wherein the inner lining layer includes a water-permeable material. A treatment layer is disposed between the inner lining layer and the outer lining layer, wherein the treatment layer includes a treatment agent.

A method is provided for bleaching teeth or dentures of a subject. The method includes providing a laminated device having a trough for the treatment of the teeth or dentures of the subject, wherein the device includes an outer layer of non-porous polymeric material in the form of a trough, an irmer layer forming an inner lining of the trough, and a treatment layer including a treatment agent disposed between the outer layer and the inner layer. An aqueous solution is added to the laminated device; and the teeth or dentures of the subject in are placed in the device.

A method of treating a tooth is provided, including capturing a treatment agent between a liner and a trough; and introducing an aqueous solution, thereby inducing the penetration of said treatment agent through said liner to treat the tooth.

A composition is provided for the whitening of a tooth including a dry form of a gel forming agent and a bleaching agent. A laminated device is provided that has a trough for the treatment of the teeth of a subject, wherein the device includes a first layer of non-porous polymeric material in the form of a trough and a premeasured amount of a composition for whitening of a tooth including a dry form of a gel forming agent and a bleaching agent.

DESCRIPTION OF THE PREFERRED EMBODIMENTS

It must be noted that as used herein and in the appended claims, the singular forms "a," "and," and "the" include plural referents unless the context clearly dictates otherwise. Thus, for example, reference to "a tooth" includes a plurality of teeth and reference to "the compound" includes reference to one or more compounds and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the trays, materials, and methodologies which are described in the publications which might be used in connection with the presently described invention. The publications discussed throughout the text are provided solely for their disclosure prior to the filing date of the present application. Nothing herein is to be construed as an admission that the inventor is not entitled to antedate such disclosure by virtue of prior invention.

The invention provides a laminated device that includes a trough for the treatment of the teeth of a subject. The device includes at least three layers: an outer layer of non-porous polymeric material in the form of a trough, an inner layer forming an inner lining of the trough, and an additional treatment layer including a treatment agent disposed between the outer layer and the inner layer. Additional layers can be included. A "laminated" device refers to a device composed of layers of materials. The layers can be fused together throughout the device, or some or all of the layers can be fused in an area which includes a majority of the area of the device. Alternatively, the layers are fused together in an area which includes a minority of the area of the device. In one embodiment, some or all of the layers are attached together at specific regions of the device and thus remain unfused throughout the majority of the surface area.

The outer layer of the device can be composed of a non-porous polymeric material and is in the form of a trough. Examples of suitable non-porous polymeric materials include but are not limited to plastics, syrene-ethylene butylene-styrene (SEBS) polymer, polystrene foam, polyethylene foam, polyurethane foam and polyolefin foam. In one embodiment, the cross-section of the trough is in a U shape. In another embodiment, the cross section embodies a V shape. In a third embodiment, the cross section embodies a flattened U shape (see FIG. 5). It should be noted that, when viewed in cross section, the trough can be laminated on one or both arms of the U, flat-bottomed U, or V shape.

Figure 1:
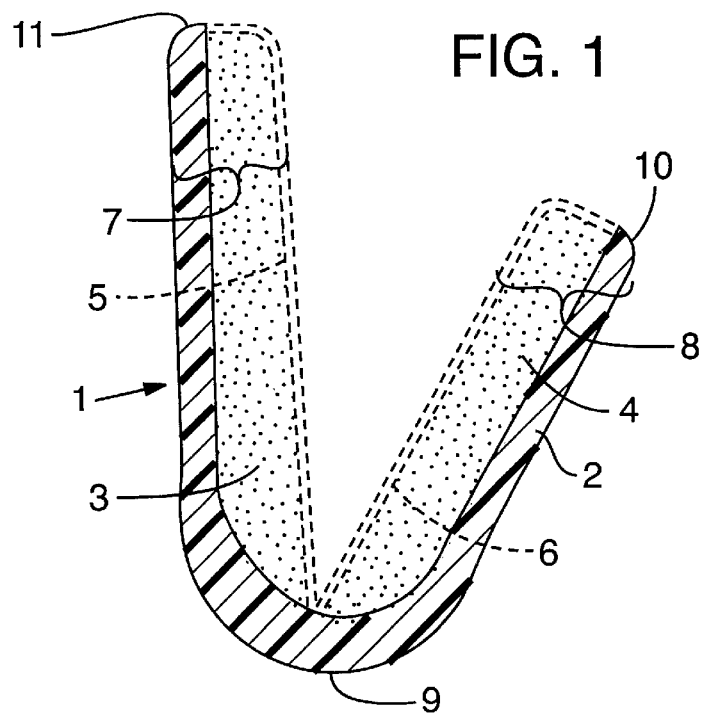
FIG. 1 shows a cross sectional view of a laminated device for the treatment of the teeth.

Referring to the drawings, the device shown in FIG. 1 has an outer non-porous polymeric layer 1, 2 that embodies a U shaped cross section with a left arm 7 and a right arm 8. In one embodiment, the non-porous polymeric layer 1, 2 is a custom splint made for a specific user. Many methods for producing such splints are well known to one of skill in the art. For example, a sheet of plastic material of the appropriate size and thickness is placed in a holder, silicone is sprayed on both sides of the sheet, and the plastic is heated on one side. The heated plastic is placed on a prepared model of the teeth or dentures to be treated. Molding putty is then pressed against the heated plastic and the sheet is contoured to the model. The model is then removed and the plastic is trimmed. Another example of preparing the plastic layer is to use an omnivac method, wherein a vacuum is used to form a plastic sheet in the shape of a subject's teeth. In another embodiment, the polymeric layer is pre-fabricated as a universal size or sizes adaptable to fit a range of variably sized teeth or dental arches. Thus, the polymeric layer is not custom fitted, but is produced as a stock tray. Many such trays are well known to one of skill in the art (e.g., U.S. Pat. No. 5,211,559, herein incorporated by reference).

As shown in FIG. 1, the device includes an inner layer on the left 5 and on the right 6 of the device which is a water permeable layer. The inner layer 5,6 can be a water permeable fabric or cloth. The cloth allows the penetration of water, but does not allow a substantial portion of a water swellable agent to pass through the cloth, as will be described in greater detail below. In one embodiment, the layer is composed of a woven fabric. A "woven" fabric is a fabric that has been prepared by interlacing fibers or threads such as on a loom. Examples of woven fabrics include silk, rayon, or cotton. In one embodiment, the woven fabric is a knit fabric. A "knit" fabric is a cloth that has been made by looping fibers or threads together. The inner layer 5, 6 can be a non-woven fabric. A specific non-limiting example of a non-woven fabric is a cloth composed of polypropylene fibers. Alternatively the inner layer 5,6 can be a thin sheet of a water impermeable material that includes holes for facilitating the passage of water. In one embodiment, the inner layer 5,6 can be a sheet of perforated plastic. In a further embodiment, inner layer 5, 6 can be a open-celled foam. In yet another embodiment, inner layer 5, 6 can be a porous film.

The inner layer 5, 6 can be either a thick or a thin lining. In one embodiment, inner layer 5,6 is thin, and is 13 mils-100 mils thick. In another embodiment, the layer is a thick layer, and is between 1–3 mm thick. In one embodiment inner layer 5, 6 is very thick, and is thicker that 3 mm (e.g., an open celled sponge). Thickness is based on the ability of the inner layer to allow the treatment agent to penetrate and to retain the water swellable agent once an aqueous solution is added (see below). One of skill in the art will be readily be able to determine an appropriate thickness of inner layer 5, 6.

Inner layer 5,6 can be stretchable, so that it can increase in surface area to cover the teeth of the subject Inner layer 5,6 can also include excess material to facilitate coverage of the teeth when a treatment layer is expanded by the addition of an aqueous solution. Thus inner layer 5, 6 can be designed to have more surface area than treatment layer 3,4 or outer layer 1,2. In this embodiment, inner layer 5,6 can have a more limited ability to stretch.

Inner layer 5,6 is attached to outer layer 1,2 so that a treatment layer 3,4 is localized between the inner 5,6 and outer 1,2 layers. In one embodiment, treatment layer 3, 4 is adjacent to outer layer 1,2. In one specific, non-limiting example, outer layer 1, 2, and treatment layer 3, 4 can be adhered with an adhesive. Treatment layer 3, 4 can be adhered to outer layer 1,2 such that a portion of the grains of treatment layer 3,4 are exposed. In this manner, when an aqueous solution is introduced the liquid penetrates inner layer 5,6, and contacts treatment layer 3,4 such that a portion of the treatment layer solubilizes. However, the aqueous solution does not penetrate outer layer 1,2. Suitable adhesives for attachment of a treatment layer 3,4 to outer layer 1,2 or inner layer 5, 6 include, but are not limited to, a glue or cement. Preferably, the glue or cement is non-toxic.

As shown in FIG. 1, inner layer 5,6 is attached to outer layer 1,2 at the inner surface of the distal ends 10, 11 of the arms of the U shape of the trough 7,8 and at the apex 9 of the trough formed by outer layer 1,2. As shown, inner layer 5,6 is attached at the inner surface of the distal ends 10, 11 of the arms of the trough 7,8; inner layer 5,6 can alternatively be attached to outer layer 1, 2 on the outer surface of the distal ends 10, 11 of the arms 7,8 of the trough. It should be noted that the attachment of inner layer 5,6 to outer layer 1,2 at the apex of the trough is optional; this attachment can be omitted. Thus inner layer 5,6 can be attached to outer layer 1,2 only at a region of the distal arms 7,8 of the trough. The attachment of inner layer 5,6 to outer layer 1,2 can be by any means known to one of skill in the art. Specific, non-limiting examples, of means of attachment include glue, cement, or a heat-seal.

Between the outer layer 1,2 of non-porous polymeric material and the inner layer 5,6 is a treatment layer 3,4 including a composition containing a treatment agent. A "treatment agent" is any composition containing a pharmaceutical, bleaching, or other dental agent, a nutrition supplement, or other biocompatible compound capable of improving the condition of the teeth or gingiva. In one embodiment the treatment agent is provided in a dry form. A "dry form" of a treatment agent is generally less than 40% water by weight. In another embodiment, a dry form is less than 5% water by weight. A treatment agent includes, but is not limited to a dental bleaching agent, an antioxidant, an anti-caries compound, a compound to decrease tooth sensitivity and an anti-microbial agent. A "bleaching agent" or "bleaching compound" is any agent or compound that whitens the teeth. Examples of suitable bleaching compounds include an oxygen radical generating agent such as metal ion free peroxides, organic peroxides, and metal ion containing peroxides. Specific, non-limiting examples of bleaching agents suitable for use with the invention are redox agents such as monopersulfate, Oxone, ammonium persulfate, potassium persulfate, potassium monopersulfate, potassium peroxymonosulfate, potassium bisulfate, potassium sulfate, and potassium peroxidisulfate. Additional specific, non-limiting examples of bleaching agents suitable for use with the device of the invention are the peroxide class of bleaching agents such as hydrogen peroxide, carbamide peroxide, urea peroxide, sodium percarbonate, sodium perborate, calcium hydroxide, potassium chlorate, magnesium carbonate and perhydrol urea. "Therapeutically effective amount of a bleaching agent" as used herein means the quantity of a the bleaching agent which, when included in the device of the invention, is necessary to whiten the teeth of a subject. A subject is any mammal, preferably a human.

Typically the dry bleaching agent is disposed in the treatment layer in amounts so that about 75% to 10% by weight of the composition of the treatment layer comprises the active bleaching agent before the addition of the aqueous solution. It should be noted that the percentage by weight of the bleaching agent can vary depending on the weight of any inactive ingredients included in the dry composition. Typically the bleaching agent is 5% to 20% by weight after the addition of the aqueous solution. Preferably, if the bleaching agent is carbamide peroxide, carbamyl peroxide or perhydrol urea, the concentration of the bleaching agent is from about 5% to about 20% by weight after the addition of the aqueous solution. More preferably, if the bleaching agent is carbamide peroxide, carbamyl peroxide, sodium percarbonate or perhydrol urea, the concentration of the bleaching agent is from about 10% to about 15% by weight after the addition of the aqueous solution.

Assays to determine a therapeutically effective amount of a bleaching agent are known in the art. For example, stained extracted teeth can be used to measure a whitening effect (see Example 1) using the device of the invention with a treatment layer including varying amounts of a bleaching agent. Other assays, such as an analysis of the effect of a bleaching agent on the soft tissues, may also be used in the determination of a therapeutically effective range of concentrations of a bleaching agent In one embodiment the treatment layer 3,4 includes a treatment agent for decreasing tooth sensitivity. The treatment agent can be any compound that lowers the susceptibility of a tooth to a stimulation such as temperature or pressure. Ingredients to decrease tooth sensitivity include, but are not limited to potassium nitrate, citric acid, citric acid salts, sodium fluoride, and strontium chloride. In another embodiment the treatment layer 3,4 includes a treatment agent that is an anti-microbial agent. Such agents are well known to one of skill in the art and include, but are not limited to, chlorhexadine, tetracycline, cetyl pyridinium chloride, benzalkonium chloride, cetyl pyridinium chloride, cetyl pyridinium bromide, methyl benzoate, and propyl benzoate.

The treatment layer 3,4 can also include palliative ingredients for periodontal tissues. Examples of such ingredients include, but are not limited to aloe, eugenol, corticosteroid and vitamin E. Pigments, sweeteners, colors, and flavors may also be incorporated into the composition. The treatment layer 3,4 can further include a gelling agent. Gelling agents include, but are not limited to an alpha starch, an agar, hydroxyethyl cellulose, mangrot seed, hydroxymethyl cellulose, and fumed aluminum silicate. The addition of these components to dental creams, such as toothpaste, are well known in the art.

The treatment layer 3,4 can include an agent for administering fluoride, such as a fluorine providing salt, which can prevent cavities. Such materials are characterized by their ability to release fluoride ions in water. Agents for administering fluoride include, but are not limited to, inorganic metal salts such as sodium fluoride, potassium fluoride, and tin fluoride such as stannous fluoride or stannous chlorofluoride, sodium fluorosilicate, ammonium fluorosilicate and sodium monofluorophosphate.

A dry, solid, water-insoluble, physiologically unobjectionable, water-swellable agent can be included in treatment layer 3,4. A "water swellable" agent is any material that increase its volume upon exposure to an aqueous solution. In one embodiment, the solution used to swell the water-swellable agent is water itself. Alternatively, the solution can be a mouthwash, a juice such as aloe vera juice, or a dilute salt solution.

In one embodiment the water-swellable agent is a polymeric sorbent. Polymeric sorbents include, but are not limited to sodium polyacrylate, sodium polyacrylamide, poly-N-vinylpyrrolidone, poly-vinyltoluenesulfonate, polysulfoethyl acrylate, poly-2-hydroxyethyl acrylate, polyvinylmethyloxazolidinone, hydrolyzed polyacrylamide, polyacrylic acid, copolymers of acrylamide and acrylic acid, and alkali metal salts of such of the polymers as contain sulfonate or carboxylate groups (see U.S. Pat. No. 3,926,891; U.S. Pat. No. 3,699,103, U.S. Pat. No. 5,693,411, all herein incorporated by reference in their entirety). In another embodiment, the water-swellable agent is a naturally occurring water-swellable agent. Such agents include, but are not limited to, mangrot seed, ground root of the buuk plant, cotton and a sponge.

The trough can be configured to treat the outer surface of the teeth, the inner surface of the teeth, or both surfaces of the teeth. In the embodiment shown in FIG. 1, the trough is configured to treat both the inner and outer surfaces of the teeth. However, in an alternate embodiment, the trough is laminated only on one arm 7 or 8 of the trough, and thus only the inner or the outer surface of the teeth will be treated with the device. For example, the trough can be configured to be laminated in a manner to treat the outer surface of the teeth, and can be composed of outer layer 1,2 treatment layer 3, and inner layer 5. Outer layer 1,2 is attached to inner layer 5 at the distal portion 11 of the left arm 7 and the apex 9 of the trough. In this configuration treatment layer 4 is omitted. However, inner layer 6 is optional. Thus the device can include outer layer 1,2, treatment layer 3, and inner layer 5, or the device can include outer layer 1,2, treatment layer 3 and inner layer 5,6.

In the alternative, the trough can be configured to treat only the inner surface of the teeth. In this embodiment the trough is composed of outer layer 1, 2, treatment layer 4, and inner layer 6. First layer 2 is attached to inner layer 6 at the distal portion 10 of the right arm 8 and at the apex 9 of the trough. In this configuration treatment layer 3 is omitted and inner layer 6 is optional. The device includes outer layer 1, 2, treatment layer 4, and inner layer 6, or outer layer 1, 2, treatment layer 4, and inner layer 5, 6. It should be noted that additional layers can be included in the device of the invention (see below).

Figure 2:
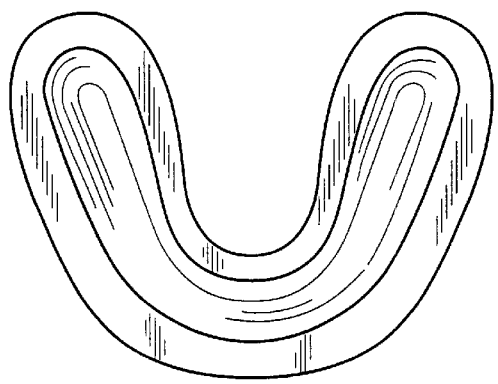
FIG. 2 is a top perspective view of a device of the invention.
Figure 3:
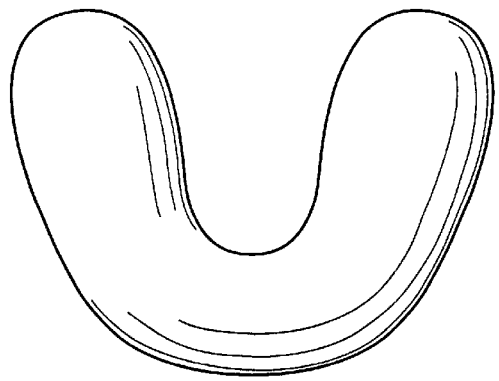
FIG. 3 is a bottom perspective view of a device of the invention.

FIG. 2 shows a top aerial view of the devices shown in cross section in FIG. 1, and illustrates an exemplary shape of the trough of the tray. FIG. 3 shows a view of the underside of the trough shown in FIG. 1.

Figure 4:
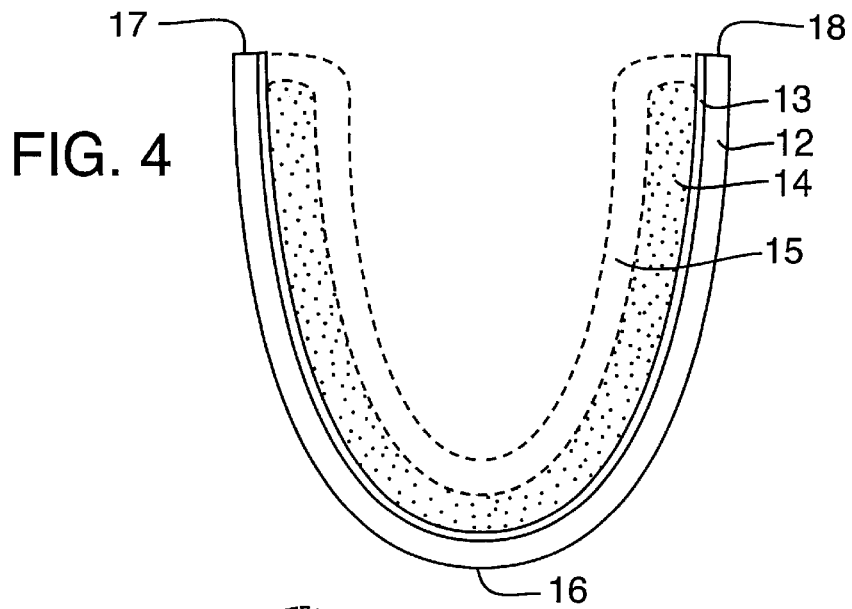
FIG. 4 shows a cross section view of another embodiment of a laminated device for the treatment of the teeth.

Referring to FIG. 4, a cross sectional view of an alternate embodiment of a U-shaped laminated device of the invention is shown. An outer layer 12 is a layer of non-porous polymeric material in the form of a trough. Outer layer 12 is proximate to an outer lining layer 13 composed of a fabric or cloth. Outer lining layer 13 can be composed of a water permeable or a water impermeable fabric. In one embodiment, outer lining layer 13 is water impermeable and is a sheet of polypropylene, polyethylene, or another plastic material. Outer lining layer 13 is attached to an inner lining layer 15 composed of a water permeable cloth. Treatment layer 14, which includes a treatment agent, is disposed between the outer lining layer 13 and the inner lining layer 15. The treatment layer 14 can also include a waterswellable agent.

It should be noted that the outer lining layer 13 is an optional layer. When outer lining layer 13 is present, the device can be configured such that the combination of outer lining layer 13, treatment layer 14, and inner lining layer 15 can be removed, and replaced. In this manner, outer layer 12 can be reused. If outer lining layer 13, treatment layer 14, and inner lining layer 15 can be removed as a unit, the means of attachment of this unit to outer layer 12 can be reusable. Means of reusable attachments are well known to one of skill in the art. An example of a reusable means of attachment is piece of Velcro, a glue that retains tackiness, or a snap. As shown in FIG. 4, outer lining layer 13 is attached to inner lining layer 15 on the inside of the ends of the arms 17, 18 of the U of the trough, thus enclosing the treatment agent included in treatment layer 14. As an alternative (not shown), inner lining layer 15 can be attached to the outer layer 12 on the side toward the interior of the trough (inside) of outer layer 12. As another alternative (not shown), inner lining layer 15 can be attached to side toward the exterior (outside) of outer layer 12 to enclose the treatment agent included in treatment layer 14.

Figure 5A:
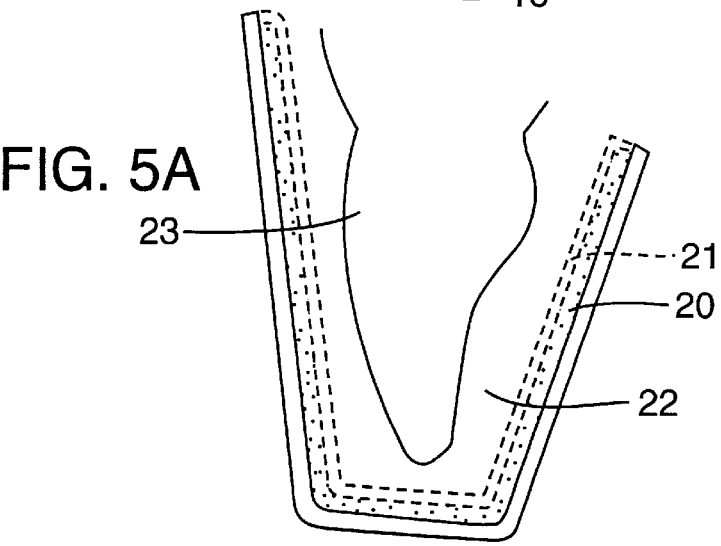
FIG. 5A is a cross sectional view of a device of the invention prior to the addition of an aqueous solution.
Figure 5B:
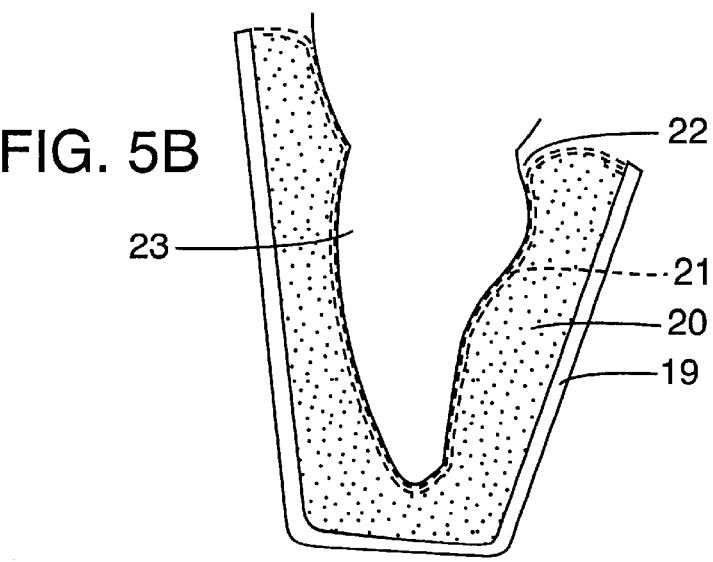
FIG. 5B is a cross sectional view of a device of the invention after the addition of an aqueous solution.

A cross section of a device of the invention is shown in FIG. 5. Outer layer 19 appears in the form of a flat bottomed U shape. Treatment layer 20 includes a treatment agent and a water swellable agent. Inner lining layer 21 is a water permeable fabric. FIG. 5A shows the device prior to the addition of water or an aqueous solution. A buffer zone 22 is present between the dental structures 23, including a tooth and surrounding gingiva, and inner lining layer 21. The dental structures 23 can be prosthetic dental structures, such as dentures. FIG. 5B shows the device after the addition of water or an aqueous solution. The water or aqueous solution penetrated the water permeable fabric of inner lining layer 21 and swelled the water swellable agent contained in treatment layer 18 such that the volume of treatment layer 20 is increased. As the volume of treatment layer 20 is increased, the buffer zone 22 between inner lining layer 21 and dental structures 23 is reduced. As shown, inner lining layer 19 now rests near or against the surface of the dental structures 23. Once the aqueous solution is added, the treatment agent contained in the treatment layer 20 penetrates the inner lining layer 21, allowing treatment of the dental structure 23.

In another embodiment, the invention also provides a composition for the whitening of a tooth including a dry form of a gel forming agent and a bleaching agent. A "dry form" of a treatment agent is generally less than 40% water by weight. In one embodiment, a dry form is less than 20% water by weight. A "bleaching agent" or "bleaching compound" is any compound which whitens teeth, as is described above. In one embodiment, the bleaching agent is an oxygen radical generating agent such as metal ion free peroxides, organic peroxides and metal ion containing peroxides. Bleaching agents suitable for use in the composition of the invention are redox agents such as monopersulfate, Oxone, ammonium persulfate, potassium persulfate, potassium monopersulfate, potassium peroxymonosulfate, potassium bisulfate, potassium sulfate and potassium peroxidisulfate. In another embodiment, bleaching agent suitable for the composition of the invention are the peroxide class of bleaching agents such as hydrogen peroxide, carbamide peroxide, urea peroxide, sodium percarbonate, sodium perborate, calcium hydroxide, potassium chlorate, magnesium carbonate and perhydrol urea.

The composition of the subject invention can also further include a catalytic agent. A "catalytic agent" is a compound or molecule which accelerates the whitening action of the bleaching compound without being consumed in the reaction. In one embodiment, the catalytic agent accelerates the release of oxygen radicals from an oxygen radical generating agent. Examples of such agents include, but are not limited to, activated charcoal, platinum, platinum salts, copper, copper salts, palladium, palladium salts, silver and silver salts. In one specific, non-limiting example, activated charcoal is used as the catalytic activator. Of particular use with the subject invention is the commercially activated charcoal Centaur, produced by Calgon, Inc. (e.g. U.S. Pat. No. 09/045,489, filed Mar., 20, 1998, herein incoporated by reference).

In one embodiment, an abrasive material can be included in the composition of the invention. For example a dicalcium phosphate abrasive may be incorporated into the composition (e.g., see U.S. Pat. No. 5, 171, 564, herein incorporated by reference). Example of dicalcium phosphate abrasives include, but are not limited to dicalcium phosphate dihydrate, anhydrous dicalcium and calcium pyrophosphate. Other abrasives for use with the subject invention include siliceous materials. Examples of such materials include, but are not limited to, silica abrasives, such as precipitated amorphous hydrated silica, and alumina abrasives, such as alumina trihydrate, aluminum silicate, calcined alumina and bentonite.

The composition can also include one or more ingredients to decrease tooth sensitivity, as described above. The composition can further include a palliative ingredient for periodontal tissues, as described above. In addition, the composition can include an antimicrobial agent or an agent for administering fluoride as an anti-caries agent, as described.

In one embodiment, the composition can include a gelling agent. A "gelling agent" is a agent which forms a semisolid suspension of small inorganic or large organic molecules upon addition of an aqueous solution The aqueous solution interpenetrates the inorganic or large organic molecules in order to form the gel. Specific, non-limiting examples of a gelling agent are an alpha starch, an agar, hydroxyethyl cellulose, mangrot seed, hydroxymethyl cellulose, sodium polyacrylate, sodium polyacrylamide, poly-N-vinylpyrrolidone, poly-vinyltoluenesulfonate, poly-sulfoethyl acrylate, poly-2-hydroxyethyl acrylate, poly-vinylmethyloxazolidinone, hydrolyzed polyacrylamide, polyacrylic acid, copolymers of acrylamide and acrylic acid and alkali metal salts of such of the polymers that contain sulfonate or carboxylate groups.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLES

Example 1

A standard flexible Styrofoam dental tray, such as is typically used in a dentist's office for fluoride treatment was prepared as an outer layer. The intaglio of the tray was coated with 0.04 gm of sodium polyacrylate. A mixture was made of 0.06 gm of sodium polyacrylate, 0.7 gm urea peroxide, 1 gm. hydroxyethylcellulose, and sufficient flavoring to impart a pleasant taste to the mixture. The mixture was evenly distributed as a treatment layer along the inner walls of the first Styrofoam layer, and compressed against the bottom and sides of the inner surface of the tray. A porous layer of flexible plastic material was sealed using a heat sensitive adhesive to the outer rim of the first Styrofoam layer to form an inner layer. As the porous flexible plastic was not elastic (it was not sufficiently stretchable), the plastic was secured with sufficient slack to allow the teeth to be inserted into the tray without compromising the integrity of the plastic sheeting, and without breaking the seal between the third layer of flexible plastic and the first layer of Styrofoam.

At the time of use, a subject filled the tray with 6 ml of water. After 30 seconds the water was absorbed by the treatment layer, and the tray was placed into the mouth covering the teeth to be whitened were covered. The tray was left in place such that the inner layer contacted the subject's teeth for ninety minutes. At the end of the wearing period, a small but clearly visible increase in whiteness of the teeth was evident. This whitening was approximately equal to 2–3 weeks of daily use of an over the counter tooth whitening paste.

Example 2

A tay was produced using a layering method similar to that described in Example 1. However, all of the sodium polyacrylate was coated as a second layer on the tray without the additional ingredients. The second layer of sodium polyacrylate was covered with an inner lining layer consisting of a thin gauze of unwoven cotton. The inner lining layer was secured to the edges of the outer layer (the Styrofoam tray). A treatment layer including urea peroxide and hydroxyethylcellulase was placed on top of the inner lining layer. The treatment layer was in turn covered with an inner lining layer of knit cotton. The inner lining layer was also secured to the edges of the first layer (the Styrofoam tray).

The dry tray was subsequently activated by the addition of mouthwash (Scope) to provide liquid and to add flavor to the other ingredients. After 30 seconds the tray was placed on a subject's teeth such that the inner lining layer rested against the teeth. The apparatus was worn for 90 minutes. A visible whitening of the teeth was noted. This whitening was approximately equal to 2–3 weeks of daily use of an over the counter tooth whitening paste.

Example 3

A custom fabricated outer layer of a dental tray was produced by vacuuforning a sheet of 0.20 inch plastic to a plastic model of a subjects teeth. The tray was trimmed to cover the teeth and very little of the surrounding tissue. A dry composition was prepared including:

1.5 gm of Oxone, a mixture including:

| | |
|---|---|
| Potassium peroxymonosulfate | 43% |
| Potassium bisulfate | 23% |
| Potassium sulfate | 29% |
| Magnesium carbonate | 2% |

0.05 gm fumed aluminum silica
0.5 gm of Pemulen (Union Carbide)
  Note: Pemulen is acrylates/C10–30 Alkyl Acrylate cross polymer, a high molecular weight co polymer of acrylic acid and a long chain alkyl methacrylate cross-linked with polyalkenyl ethers of polyalcohols)
flavoring (sufficient for a pleasant taste)
Just prior to use, 6 ml of water was added to the dry composition. The pH was adjusted to approximately 7.5.

The mixture was stirred for 30 seconds. One-third of the wetted composition was placed into the custom fabricated tray and the tray was subsequently placed over a subject's teeth. After 90 minutes, the tray was removed. A visible amount of whitening of the subject's teeth had occurred. This whitening was approximately equal to 2–3 weeks of daily use of an over the counter tooth whitening paste.

Example 4

A custom fabricated tray was prepared as described in Example 3. A dry mixture was prepared including:

0.1 gm sodium polyacrylate 0.7 gm urea peroxide 1.0 gm hydroxyethylcellulose flavoring (sufficient to impart a pleasant taste)

The dry mixture was placed as a treatment layer in the custom fabricated tray. Aloe vera juice was placed in the tray. The addition of the aloe vera juice activated the bleaching agent. The tray was placed over the subject's teeth, and worn for 90 minutes. Visible whitening was noticed at the end of the treatment period.

Example 5

A dry powdered mixture was prepared in the following proportions:

1.5 gm of Oxone, a mixture including:

| Potassium peroxymonosulfate | 43% |
|---|---|
| Potassium bisulfate | 23% |
| Potassium sulfate | 29% |
| Magnesium carbonate | 2% |

2.24 gm tripoly phosphate 0.1 gm fumed aluminum silica 0.5 gm of Permulen (Union Carbide)

0.3 gm potassium nitrate sufficient flavoring to impart a pleasant taste and color.

A toothbrush was dipped into the powder to coat the brush. Upon making contact with the moisture in the toothbrush and with the subject's saliva the whitening agent became active. A subject brushed their teeth using the composition; the procedure was repeated three times in three minutes. At the end of fifteen sessions a visible difference was evident in the brightness of the teeth.

Example 6

A standard flexible Styrofoam dental tray, such as is typically used in a dentist's office for fluoride treatment was prepared as an outer layer. A treatment agent was applied on the surface of the Styrofoam tray. The surface of the treatment agent was covered with non-woven polypropylene, and heat sealed by heating the polypropylene to 375° F. at the outer edge of the Styrofoam dental tray. The resulting laminate was heated to 300° F. and vacuformed or pressure molded into the final shape of the trough.

Example 7

Injection molding was used to prepare an outer layer consisting of a dental tray from a non-porous polymeric material, using methods well known to one of skill in the art. A non-woven polypropylene fabric was used as an inner lining layer and was attached at the apex of the trough using a heat seal technique (see Example 6). Similarly, the polyproylene fabric was sealed on the ends of the alms of the trough, leaving two pockets formed by the fabric and the inner wall of the dental tray. The treatment agent was then injected inside the pockets, and the fabric was then sealed along the rim of the tray so that in the dry state the treatment agent was retained between the polypropylene fabric and the polymeric material of the outer layer.

Additional trays were made using adhesive to adhere the fabric to the non-porous polymeric material of the outer layer. A non-toxic hot glue was used to adhere the fabric of the inner lining layer to the non-porous polymeric material of the outer layer.

Example 8

A laminated fabric was produced by placing a dry treatment agent between two sheets of woven fabric. The edges of the fabric were sealed such that the treatment agent was retained between them without significant leakage. The laminated fabric was then placed over the raised (male) portion of a tray mold. A sheet of foam material was vacuformed over the laminated fabric. The fabric was adhered to the tray using a heat sealing procedure, and excess fabric outside the vacuformed form was removed.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for the treatment of teeth, comprising:

an outer layer of non-porous polymeric material forming a trough;

an inner layer forming an inner lining of said trough; and a treatment layer comprising a treatment agent encased between said outer layer and said inner layer, wherein said inner layer allows penetration of said treatment agent through said inner layer after an aqueous solution is introduced to said device and wherein said inner layer does not allow a substantial portion of said treatment agent to pass through said inner layer before said aqueous solution is introduced, wherein said treatment agent is a bleaching agent, and said treatment agent is in dry solid powder form thereby avoiding a leakage problem of dental trays filled with gel or liquid treatment agents.

2. The device of claim 1, wherein said bleaching agent is a redox agent in dry form.

3. The device of claim 2, wherein said redox agent is selected from the group consisting of monopersulfatc, Oxone, ammonium persulfate, potassium persulfate, potassium monopersulfate, potassium peroxymonosulfate, potassium bisulfatc, potassium sulfate and potassium peroxidisulfate.

4. The device of claim 1, wherein said bleaching agent is a bleaching agent of the peroxide class in dry form.

5. The device of claim 4, wherein said bleaching agent is selected from the group consisting of hydrogen peroxide, carbamide peroxide, urea peroxide, sodium percarbonate, sodium perborate, calcium hydroxide, potassium chlorate, magnesium carbonate and perhydrol urea.

6. The device of claim 1, wherein said treatment layer further comprises a gelling agent in dry form.

7. The device of claim 6, wherein said gelling agent is selected from the group consisting of an alpha starch, an agar, hydroxyethyl cellulose, mangrot seed, hydroxymethyl cellulose and fumed aluminum silicate.

8. The device of claim 1, wherein said treatment layer further comprises a dry, solid, water-insoluble, physiologically unobjectionable water-swellable agent.

9. The device of claim 8, wherein said water-swellable agent is a polymeric sorbent.

10. The device of claim 9, wherein said polymeric sorbent is selected from the group consisting of sodium polyacrylate, sodium polyacrylamide, poly-N-vinylpyrrolidone, poly-vinyltoluenesulfonate, poly-sulfoethyl acrylate, poly-2-hydroxyethyl acrylate, poly-vinylmethyloxazolidinone, hydrolyzed polyacrylamide, polyacrylic acid, copolymers of acrylamide and acrylic acid and alkali metal salts of said polymers as contain sulfonate or carboxylate groups.

11. The device of claim 8, wherein said water swellable agent is a naturally occurring water-swellable agent.

12. The device of claim 11, wherein said naturally occurring water swellable agent is selected from the group consisting of mangrot seed, ground root of the bunk plant, cotton, and a sponge.

13. The device of claim 1, wherein said treatment layer further comprises a palliative ingredient for periodontal tissues in dry form.

14. The device of claim 13, wherein said palliative agent is selected from the group consisting of aloe, eugenol, corticosteroid and vitamin E.

15. The device of claim 1, wherein said treatment layer further comprises an agent for administering fluoride in dry form.

16. The device of claim 1, wherein said treatment layer further comprises an ingredient to decrease tooth sensitivity in dry form.

17. The device of claim 16, wherein said ingredient to decrease tooth sensitivity is derived from a member of the group consisting of potassium nitrate, citric acid, citric acid salts, sodium fluoride, and strontium chloride.

18. The device of claim 1, wherein said treatment layer further comprises a flavoring agent in dry form.

19. The device of claim 1, wherein said treatment layer further comprises an anti-microbial agent in dry form.

20. The device of claim 1, wherein said antimicrobial is selected from the group consisting of chlorhexadine, tetracycline, cetyl pyridinium chloride, benzalkonium chloride, cetyl pyridinium chloride, cetyl pyridinium bromide, methyl benzoate, and proply benzoate.

21. The device of claim 1, wherein said inner layer is malleable and can stretch to the contours of the teeth of a subject.

22. The device of claim 1, wherein said inner layer is a perforated plastic sheet.

23. The device of claim 1, wherein said inner layer is a cloth permeable to said treatment agent.

24. The device of claim 1, wherein said cloth comprises polypropylene fibers.

25. The device of claim 1, wherein said outer layer, treatment layer and inner layer are continuous throughout the trough.

26. The device of claim 1, wherein said outer layer, treatment layer and inner layer are not continuous throughout the form of the trough.

27. The device of claim 1, wherein said teeth are prosthetic teeth.

28. The device of claim 1, wherein said teeth include surrounding gingival tissue.

29. A device for treatment of teeth, comprising:
 an outer layer of non-porous polymeric material in the form of a trough, wherein said trough has an outside and an inside surface;
 an outer lining layer proximate to said inside surface of said outer layer, said outer lining layer comprising a material for retaining a treatment agent;
 an inner lining layer forming an inner lining of said trough, wherein said inner lining layer comprises a water-permeable material; and
 a treatment layer encased between said inner lining layer and said outer lining layer, wherein said treatment layer comprises a treatment agent, wherein said treatment agent is a bleaching agent, and said treatment agent is in dry solid powder form thereby avoiding a leakage problem of dental trays filled with gel or liquid treatment agents.

30. The device of claim 29, wherein said outer lining layer is adjacent to said inside surface of said outer layer.

31. A method for bleaching teeth or dentures of a subject, comprising:
 providing a laminated device having a trough for the treatment of the teeth of a subject, wherein said device comprises an outer layer of non-porous polymeric material in the form of a trough, an inner layer forming an inner lining of said trough, and an additional treatment layer comprising a treatment agent encased between said outer layer and said inner layer, wherein said treatment agent is a bleaching agent, and wherein said treatment agent is in dry solid powder form thereby avoiding a leakage problem of dental trays filled with gel or liquid treatment agents;
 adding an aqueous solution to said laminated device; and
 placing the teeth or dentures of said subject in said device.

32. The device of claim 1, wherein said device is adaptable to fit a range of variously sized sets of teeth.

33. The device of claim 1, wherein said outer lining layer is a water permeable material.

* * * * *